US005856330A

United States Patent [19]
Müllner et al.

[11] Patent Number: 5,856,330
[45] Date of Patent: Jan. 5, 1999

[54] USE OF XANTHINE DERIVATIVES FOR THE INHIBITION OF DEPHOSPHORYLATION OF COFILIN

[75] Inventors: Stefan Müllner, Hochheim; Claudia Dax, Gernsheim, both of Germany

[73] Assignee: Hoechst Aktiengesellschaft, Frankfurt am Main, Germany

[21] Appl. No.: 899,023

[22] Filed: Jul. 23, 1997

[30] Foreign Application Priority Data

Jul. 31, 1996 [DE] Germany .......... 196 30 837.2
Oct. 1, 1996 [DE] Germany .......... 190 40 556.4

[51] Int. Cl.$^6$ .................. A61K 31/52
[52] U.S. Cl. .......... 514/263; 514/264; 514/907
[58] Field of Search .......... 514/263, 264, 514/907

[56] References Cited

U.S. PATENT DOCUMENTS

| | | | |
|---|---|---|---|
| 3,737,433 | 6/1973 | Mohler et al. ............ | 544/271 |
| 4,061,767 | 12/1977 | Ertel et al. ............... | 424/282 |
| 4,108,995 | 8/1978 | Mohler et al. ............ | 424/253 |
| 4,833,146 | 5/1989 | Gebert et al. ............. | 514/263 |
| 5,240,960 | 8/1993 | Hambleton et al. ........ | 514/521 |
| 5,308,865 | 5/1994 | Bartlett et al. ............ | 514/465 |

FOREIGN PATENT DOCUMENTS

| | | |
|---|---|---|
| 0 279 079 A2 | 8/1988 | European Pat. Off. . |
| 0 514 789 | 11/1992 | European Pat. Off. . |
| 0 528 164 | 2/1993 | European Pat. Off. . |
| 0 547 508 | 6/1993 | European Pat. Off. . |
| 0 557 876 | 9/1993 | European Pat. Off. . |
| 0 665 013 A1 | 8/1995 | European Pat. Off. . |
| WO 92/07566 | 5/1992 | WIPO . |
| WO 95/10282 | 4/1995 | WIPO . |
| WO 96/20710 | 7/1996 | WIPO . |

OTHER PUBLICATIONS

R. Turner, "Use of xanthine derivs. esp. . . . pentoxifyllilne . . . for inhibiting interleuken–8 elaboration and treating a symptom of an upper respiratory viral infection, esp. a rhinovirus infection", Derwent abstract No. 96–151131 for WO 96/05836, (1996).

P. Dugel et al., "Treatment of AIDS–associated optic neuropathy–by oral admin. of . . . pentoxifylline . . . and other tumour necrosis factor blockers", Derwent abstract No. 93–320439 for WO 93/18770, (1993).

J. Bianco et al., "Modulation of cellular response using substd. xanthine (s) — for prevention of bone marrrow rejection and treatment of tumours, leukaemia, bacterial, viral, fungal or protozoal infection, etc.", Derwent abstract No. 92–433353 for WO 92/21344, (1992).

D. Steiffge et al., "Use of . . . pentoxifylline . . . in medicaments–for treating inflammatory disorders", Derwent abstract No. 90–024285 for EP 0 351 885, (1990).

CA 123:160563, Mentz et al. 1995.

Primary Examiner—Kimberly Jordan
Attorney, Agent, or Firm—Finnegan, Henderson, Farabow, Garrett & Dunner, L.L.P.

[57] ABSTRACT

Compounds of the formula I where one of the radicals $R^1$ and $R^3$ is a radical of the formula II —$(CH_2)_n$—A—$CH_3$ (II) in which A is a covalent bond, —C(O)— or —C($R^4$)(OH)—, are suitable for the production of pharmaceuticals for the modulation of apoptosis. A combination preparation comprising a compound of the formula I and a compound of the formula IV and/or V is suitable for the production of pharmaceuticals for the modulation of apoptosis.

9 Claims, No Drawings

USE OF XANTHINE DERIVATIVES FOR THE INHIBITION OF DEPHOSPHORYLATION OF COFILIN

In contrast to necrosis, apoptosis is a genetically controlled (programmed) cell death, which is an essential constituent of the life of multicellular organisms.

In contrast to this apoptosis process which is normal and necessary to life, numerous forms of illness or their symptoms are an expression of an abnormal, i.e. a) uncontrolled or b) suppressed apoptosis [a): infarct, stroke or neurodegeneration, b) hypertrophic disorders]. Healing processes of illnesses can thus be possible by means of suppression or activation of apoptosis (e.g. transverse lesion of the spinal cord, immune defense etc.). Apoptosis proceeds after induction of defined death signals, for example by stimulation of certain receptors (e.g. Fas receptor), via a secondarily induced complex cascade of intermeshing biochemical events, at the end of which is the disintegration of the intact cell to give membrane-packed units, which can be disposed of by the body without or only with slight damage to the surrounding cells (opposite to necrosis). In some cases here the transitions between necrosis and apoptosis are fluid; thus there are cases in which necrosis leads to apoptosis (or conversely) (e.g. infarct, stroke etc.).

As a costimulatory factor in T cells, cofilin, a 19 kDa actin-binding protein, plays a crucial part in the immune reaction. Cofilin is present in the cytosol in phosphorylated form and is transported into the cell nucleus after dephosphorylation. It obviously serves here as a transport molecule for the protein actin, which has no nuclear recognition sequence and is known as a DNAse I inhibitor. By means of this mechanism, the degree of phosphorylation of the cytosolic cofilin can bring a regulating and modulating influence to bear on the apoptosis of cells [J. of Immunology, 156, 4167–4173 (1996)].

It has now been found that certain xanthine derivatives are suitable for inhibiting the dephosphorylation of cofilin and thus they have a modulating influence on apoptosis.

The invention therefore relates to the use of at least one xanthine derivative of the formula I

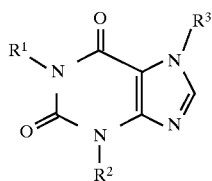

(I)

and/or an optionally stereoisomeric form of the xanthine derivative of the formula I,
where
R is $(C_1–C_4)$-alkyl,
one of the radicals $R^1$ or $R^3$ is a radical of the formula II

(II)

in which R
  a) is a covalent single bond and in which n is the integer zero, 1, 2, 3, 4, 5, 6 or 7,
  b) is a radical —CO— and in which n is the integer 1, 2, 3, 4, 5 or 6, or
  c) is a radical —C($R^4$)(OH)— and in which n is the integer 1, 2, 3, 4, 5 or 6 and
$R^4$ is
  a) a hydrogen atom or
  b) $(C_1–C_3)$-alkyl, and the other radical $R^3$ or $R^1$ is
  a) a hydrogen atom,
  b) $(C_1–C_7)$-alkyl,
  c) $(C_4–C_8)$-cycloalkylalkyl or
  d) alkyl having 2 to 6 carbon atoms, in which the carbon chain is interrupted by an oxygen atom,
for the preparation of pharmaceuticals for the modulation of apoptosis.

Xanthine derivatives of the formula I are preferably employed where
$R^2$ is $(C_1–C_4)$-alkyl and
one of the radicals $R^1$ or $R^3$ is a radical of the formula II, in which R is
  a) a radical —CO— or
  b) a radical —C($R^4$)(OH)—, and n is the integer 3, 4, 5 or 6 and
$R^4$ is a hydrogen atom or $(C_1–C_3)$-alkyl and
the other radical $R^3$ or $R^1$ is $(C_1–C_7)$-alkyl or $(C_4–C_8)$-cycloalkylalkyl.

Xanthine derivatives of the formula I are particularly preferably employed where
$R^2$ is $(C_1–C_2)$-alkyl,
$R^1$ is the radical of the formula II, in which R is
  a) a radical —CO— or
  b) a radical —C($R^4$)(OH)—, and n is the integer 3, 4, 5 or 6 and
$R^4$ is a hydrogen atom or $(C_1–C_2)$-alkyl and
$R^3$ is $(C_1–C_7)$-alkyl or $(C_4–C_8)$-cycloalkylalkyl.

Xanthine derivatives of the formula I are in particular preferably employed where
$R^2$ is $(C_1–C_2)$-alkyl,
$R^1$ is a radical of the formula II in which R is
  a) a radical —CO— or
  b) a radical —C($R^4$)(OH)—, and n is the integer 3, 4, 5 or 6 and
$R^4$ is a hydrogen atom or $(C_1–C_2)$-alkyl and
$R^3$ is $(C_2–C_5)$-alkyl or $(C_4–C_6)$-cycloalkylalkyl.

1-(5-Hydroxy-5-methylhexyl)-3-methyl-7-propylxanthine is very particularly preferably used.

The alkyl radicals of the formula I are straight-chain or branched. The expression "$(C_4–C_8)$-cycloalkylalkyl" defines those alkyl radicals which are substituted by $(C_3–C_6)$- cycloalkyl, the sum of all carbon atoms being less than or equal to 8. These include, for example, the cyclopropylmethyl to -pentyl, cyclobutylmethyl to -butyl, cyclopentylmethyl to -propyl and cyclohexylmethyl and -ethyl radicals. The radical "(O)" is an oxygen atom.

"Modulation of apoptosis" is understood as meaning the inhibition or induction of apoptosis.

As used herein, the term "therapeutically effective amount" means an amount of the compound which is effective in treating the named disorder. A therapeutically effective amount can be readily determined by the attending diagnostician, as one skilled in the art, by the use of known techniques and by observing results obtained under analogous circumstances.

As used herein, the term "patient" refers to a mammal such as a dog, cat, guinea pig, mouse, rat or human being.

The terms "treating" or "to treat" means to alleviate symptoms, eliminate the causation either on a temporary or permanent basis, or to prevent or slow the appearance of symptoms of the named disorder.

The xanthine derivatives of the formula I are prepared by known processes (U.S. Pat. No. 3,737,433; U.S. Pat. No. 4,108,995; U.S. Pat. No. 4,833,146), the disclosures of which are herein incorporated by reference.

One procedure consists, for example, in alkylating a 3-alkylxanthine of the formula Ia

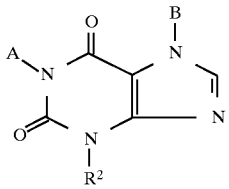

in which

R² is an alkyl group having 1 to 4 carbon atoms,

A is a hydrogen atom, $(C_4-C_8)$-cycloalkylalkyl, $(C_2-C_6)$-alkoxyalkyl or the radical of the formula II and B is a hydrogen atom, $(C_4-C_8)$-cycloalkylalkyl, $(C_2-C_6)$-alkoxyalkyl, the radical of the formula II, or a benzyl or diphenyl radical, but where at least one of these radicals A and B is a hydrogen atom, directly or in the presence of a basic condensing agent or in the form of one of its salts in the 1- and/or 7-position in one step or stepwise using appropriate alkylating agents of the formula III

in which

X is a halogen atom or a sulfonic acid ester or phosphoric acid ester group and

Q is $(C_4-C_8)$-cycloalkylalkyl, $(C_2-C_6)$-alkoxyalkyl or a radical of the formula II, with subsequent reductive removal of the radical B if this is a benzyl or diphenylmethyl group, or optionally hydrolytic elimination of an alkoxy methyl radical from the position of the radical B and/or reduction of the keto group to the alcohol function if A or B is an oxoalkyl radical, at a reaction temperature between 0° C. and the boiling point of the reaction medium used in each case.

The starting substances of the reactions are known or can be easily prepared by methods known from the literature.

The present invention provides a method for inhibiting the dephosphorylation of the protein cofilin comprising administering to a patient in need thereof a therapeutically effective amount of a compound of the formula I and/or an optionally stereoisomeric form of the compound of the formula I and/or a physiologically tolerable salt of the compound of the formula I.

Due to the pharmacological properties of the xanthine derivatives of the formula I, these compounds can be employed for the specific modulation of apoptosis. The present invention therefore also provides a method of treating a disorder with uncontrolled apoptosis in a patient comprising administering a therapeutically effective amount of a compound of formula I and/or an optionally stereoisomeric form of the xanthine derivative of the formula I and or a physiologically tolerable salt of the compound of formula I. Disorders with uncontrolled apoptosis are, for example, infarct, myoma, muscular atrophy, muscular dystrophy, cachexia, systemic inflammation response syndrome (SIRS), adult respiratory distress syndrome (ARDS), cerebral malaria, chronic pneumonia, pulmonary sarcosidosis, reperfusion damage, scar formation, enteritis, acquired immune deficiency syndrome (AIDS), cancer, disorders with an increased protein loss, stroke, neurodegeneration, chronic renal insufficiency, burn injuries or hypertrophic disorders.

The present invention further provides a pharmaceutical composition effective for use in the treatment of a disorder with uncontrolled apoptosis comprising at least one xanthine derivative of the formula I and/or an optionally stereoisomeric form of the compound of the formula I and/or a physiologically tolerable salt of the compound of the formula I as active substance. The pharmaceutical composition can be administered according to the present invention in any suitable form or mode which makes the compound bioavailable in effective amounts. The pharmaceutical composition may be administered with a physiologically tolerable excipients, diluents and/or other active compounds and auxiliaries.

The pharmaceuticals according to the invention are administered parenterally, orally or rectally or, if appropriate, also applied topically.

Suitable solid or liquid pharmaceutical preparation forms are, for example, granules, powders, coated tablets, tablets, (micro)capsules, suppositories, sirups, juices, suspensions, emulsions, drops or injectable solutions and also preparations with sustained release of active compound, in whose preparation customary auxiliaries, such as excipients, disintegrants, binders, coating agents, swelling agents, glidants or lubricants, flavorings, sweeteners or solubilizers, are used. Frequently used auxiliaries which may be mentioned are, for example, magnesium carbonate, titanium dioxide, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, e.g. glycerol.

The identification of those patients who would benefit from the present invention is well within the ability and knowledge of one skilled in the art. A clinician skilled in the art can readily identify, by the use of clinical tests, physical examination and medical/family history, those patients who are suffering from a disorder with uncontrolled apoptosis.

Preferably, the pharmaceutical preparations are prepared and administered in dose units, each unit containing as active constituent a certain dose of at least one xanthine derivative of the formula I. With solid dose units such as tablets, capsules, coated tablets or suppositories, this dose is up to approximately 1000 mg, but preferably approximately 100–600 mg, and with injection solutions in ampoule form up to 300 mg, preferably 20–200 mg. For the treatment of a patient (70 kg), in early phases an intravenous infusion treatment of 100–2000 mg per day is indicated. In the the later rehabilitation phase, an oral administration of 3 times 400 mg per day, in particular of 1-(5-hydroxy-5-methylhexyl)-3-methyl-7-propylxanthine, is indicated.

Under certain circumstances, however, even higher or lower doses are appropriate. The administration of the dose can be carried out either by single administration in the form of an individual dose unit or else of several smaller dose units or by repeated administration of subdivided doses at certain intervals.

Finally, xanthine derivatives of the formula I and/or, if appropriate, their corresponding salts, can also be administered together with a therapeutically effective amount of other suitable active compounds, for example active compounds which trap free oxygen radicals, e.g. 1,5-dihydro-4H-pyrazolo(3,4-d)pyrimidin-4-one, superoxide dismutase, dimethyl sulfoxide or mannitol, heparin, ascorbic acid or deferoxamine.

Furthermore, a combination preparation comprising a xanthine derivative of the formula I and a compound of the formula IV or V shows a superadditive inhibitory effect on the dephosphorylation of cofilin and thus on the activation of cofilin, which leads to a modulation of apoptosis. Due to the extent of this effect, the use of this combination preparation can be extended to areas which until now were closed, for example, to an immunosuppressant therapy by the individual components.

Accordingly, the present invention relates to a composition having a synergistic inhibitory effect on the dephosphorylation of cofilin which comprises 1) a synergistically effective amount of at least one xanthine derivative of the formula I as defined above, and
2) a synergistically effective amount of a compound of the formula IV and/or V,

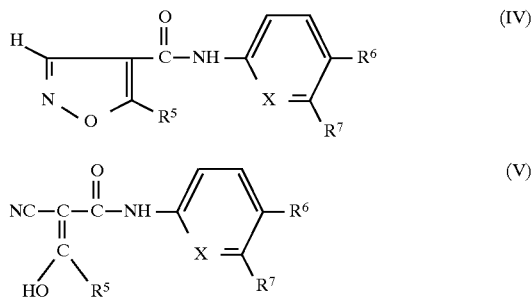

and/or an optionally stereoisomeric form of the compound of the formula IV or V and/or a physiologically tolerable salt of the compound of the formula IV or V, where $R^5$ is
 a) $(C_1-C_4)$-alkyl,
 b) $(C_3-C_5)$-cycloalkyl,
 c) $(C_2-C_6)$-alkenyl or
 d) $(C_2-C_6)$-alkynyl, $R^6$ is
 a) —$CF_3$,
 b) —O—$CF_3$,
 c) —S—$CF_3$,
 d) —OH,
 e) —$NO_2$,
 f) halogen,
 g) benzyl,
 h) phenyl,
 i) —O-phenyl,
 k) —CN or
 l) —O-phenyl, mono- or polysubstituted by
  1) $(C_1-C_4)$-alkyl,
  2) halogen,
  3) —O—$CF_3$ or
  4) —O—$CH_3$, $R^7$ is
 a) $(C_1-C_4)$-alkyl,
 b) halogen, or
 c) a hydrogen atom, and X is
 a) a —CH group or
 b) a nitrogen atom.

This invention also relates to a process for preparing such a composition which comprises combining synergistically effective amounts of the two components.

In another embodiment the invention relates to an improved process for treating disorders with uncontrolled apoptosis in a patient comprising administering (1) a therapeutically effective amount of at least one xanthine derivative of the formula I, in conjunctive therapy with (2) a therapeutically effective amount of at least one compound of the formula IV and/or V.

In yet another embodiment, the invention relates to an improved method for inhibiting the dephosphorylation of the protein cofilin comprising administering to a patient in need thereof (1) a therapeutically effective amount of at least one xanthine derivative of the formula I, in conjunctive therapy with (2) a therapeutically effective amount of at least one compound of the formula IV and/or V.

A further aspect of the invention resides in a therapeutic combination preparation for use in the treatment of disorders with uncontrolled apoptosis which comprises (1) a therapeutically effective amount of at least one xanthine derivative of the formula I, (2) a therapeutically effective amount of at least one compound of formula IV and/or V, and (3) a physiologically acceptable excipient and further suitable active compounds, additives or auxilliaries.

The use is preferred of a compound of the formula IV and/or V and/or an optionally stereoisomeric form of the compound of the formula IV or V and/or a salt of the compound of the formula IV or V, where $R^5$ is
 a) methyl,
 b) cyclopropyl or
 c) $(C_3-C_5)$-alkynyl, $R^6$ is —$CF_3$ or —CN,
$R^7$ is a hydrogen atom or methyl, and
X is a —CH— group, in combination with xanthine derivatives of the formula I, where $R^2$ is $(C_1-C_2)$-alkyl,
$R^1$ is a radical of the formula II, in which R is
 a) a radical —CO—, or
 b) a radical —$C(R^4)(OH)$—, and n is the integer 3, 4, 5 or 6 and $R^4$ is a hydrogen atom or $(C_1-C_2)$-alkyl and
$R^3$ is $(C_2-C_5)$-alkyl or $(C_4-C_6)$-cycloalkylalkyl.

The use is in particular preferred of N-(4-trifluoromethylphenyl)-2-cyano-3-hydroxycrotonamide, 2-cyano-3-cyclopropyl-3-hydroxyacrylic acid (4-cyanophenyl)amide or N-(4-trifluoromethylphenyl)-2-cyano-3-hydroxyhept-2-en-6-ynecarboxamide in combination with 1-(5-hydroxy-5-methylhexyl)-3-methyl-7-propylxanthine.

The preparation of the compound of the formula IV or V is carried out according to known processes, such as are described in EP 484 223; EP 529 500; U.S. Pat. No. 4 061 767; EP 538 783 or EP 551 230, the disclosures of which are herein incorporated by reference. The starting substances for the chemical reactions are known or can be easily prepared by methods known from the literature.

The term "alkyl," "alkenyl" or "alkynyl" is understood as meaning radicals whose carbon chain can be straight-chain or branched. Furthermore, the alkenyl or alkynyl radicals can also contain one or more double bonds or one or more triple bonds. Cyclic alkyl radicals are, for example, 3- to 5-membered monocycles such as cyclopropyl, cyclobutyl or cyclopentyl. The term "superadditive" is understood as meaning actions which are greater than the sum of the individual actions. As used herein, the term "synergistically effective amount" refers to the amount of each component of the combination preparation which is effective in producing more than the additive effect of each component. As used herein, the term "conjunctive therapy" contemplates co-administration of a xanthine derivative of formula I along with a compound of formula IV and/or V. This co-administration may take place at essentially the same time, it may take place sequentially, or it may take place alternately.

In providing co-administration at essentially the same time, the courses of treatment with a xanthine derivative of formula I and a compound of formula IV and/or V run essentially concomitantly. In providing sequential co-administration, a full course of treatment of one of the agents is terminated and then followed by a full course of treatment of the other. In providing alternate co-administration, a partial course of treatment of one of the agents is terminated and then followed by a partial course of treatment of the other in an alternating manner until a full treatment of each agent is administered.

The therapeutic combination preparation according to the present invention is suitable for the treatment of disorders with uncontrolled apoptosis. Disorders with uncontrolled apoptosis for which the therapeutic combination preparation is suitable are, for example, transplants, autoimmune disorders, infarct, stroke, inflammations, neurodegeneration, myoma, muscular atrophy, muscular dystrophy, cachexia, systemic inflammation response syndrome (SIRS), adult respiratory distress syndrome (ARDS), cerebral malaria, chronic pneumonia, pulmonary sarcosidosis, reperfusion damage, scar formation, enteritis, burn damage, acquired immune deficiency syndrome (AIDS), cancer, disorders with increased protein loss, chronic renal insufficiency or hypertrophic disorders.

The therapeutic combination preparation according to the invention can also include compositions or combination packs in which the constituents are placed next to one another and can therefore be used simultaneously, separately or at time intervals in one and the same human or animal body.

The therapeutic combination preparation according to the invention can be a dose unit in a suitable administration form such as capsules (including microcapsules, which in general contain no pharmaceutical excipients), tablets including coated tablets and pills or suppositories, where when using capsules, the capsule material can assume the function of the excipient and the contents can be present, for example, as a powder, gel, solution, emulsion or dispersion. It is particularly advantageous and simple, however, to prepare oral or peroral formulations containing the two active compound components 1) and 2) which contain the calculated amounts of the active compounds together with any desired pharmaceutical excipient. An appropriate formulation (suppository) for rectal therapy can also be used. Likewise, transdermal administration in the form of ointments or creams, parenteral (intraperitoneal, subcutaneous, intramuscular) injection or oral administration of solutions which contain the combinations according to the invention is possible. Beside the active compounds, ointments, pastes, creams and powders can contain the customary excipients, e.g. animal and vegetable fats, waxes, paraffins, starch, tragacanth, cellulose derivatives, polyethylene glycols, silicones, silicic acid, aluminum hydroxide, talc, zinc oxide, lactose, bentonite, calcium silicate and polyamide powder or mixtures of these substances. The tablets, pills or granules can be prepared by processes such as pressing, dipping or fluidized-bed processes or pan coating and contain excipients and other customary auxiliaries such as gelatin, agarose, starch (e.g. potato, corn or wheat starch), cellulose such as ethylcellulose, silica, magnesium carbonate, various sugars such as lactose and/or calcium phosphate. The coating solution usually consists of sugar and/or starch sirup and usually also contains gelatin, synthetic cellulose esters, gum arabic, polyvinylpyrrolidone, pigments, surface-active substances, plasticizers and similar additives well known in the art. For the production of the preparation forms, any customary flow-regulating agent, lubricant or glidant, such as magnesium stearate, and separating agent can be used.

Preferably, the preparations have the form of coat/core tablets or multilayer tablets, the active component 2 being in the coat or in the core or in one layer, while the active component 1 is in the core, in the coat or in another layer. The active compound components can also be present in sustained-release form or adsorbed onto depot material or included in depot material (e.g. cellulose or polystyrene resin basis, (e.g. hydroxyethylcellulose). A delayed release of the active compounds can also be achieved by providing the layer or the compartment concerned with customary enteric coatings. The dose to be used is of course dependent on various factors such as the living being to be treated (i.e. human or animal), age, weight, general state of health, the degree of severity of the symptoms, the disorder to be treated, possible concomitant disorders (if present), the nature of the concomitant treatment with other pharmaceuticals, or frequency of the treatment. The doses are in general administered several times per day and preferably once to three times per day. The amounts of individual active compound used are based in this case on the recommended daily dose of the respective individual active compound and in general in the combination preparation should be from 10% to 100% of the recommended daily dose, preferably from 20% to 80%, in particular 50%. Suitable therapy with the combinations according to the invention thus consists, for example, in the administration of one, two or 3 individual doses of the preparation consisting of N-(4-trifluoromethylphenyl)-2-cyano-3-hydroxycrotonamide sodium salt in an amount from 2 mg to 250 mg, preferably 5 mg to 150 mg, in particular 10 mg to 50 mg, particularly preferably 10 mg to 20 mg and 1-(5-hydroxy-5-methylhexyl)-3-methyl-7-propylxanthine in an amount from 100 to 600 mg, in particular from 150 to 300 mg, preferably from 20 to 200 mg.

The disclosures of German Application Ser. Nos. 19630837.2 filed Jul. 31, 1996 and 19640556.4 filed Oct. 1, 1996, are herein incorporated by reference.

EXAMPLE 1

Preparation of 1-(5-hydroxy-5-methylhexyl)-3-methyl-7-propylxanthine

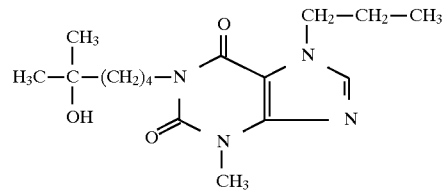

22.4 g (0.3 mol) of methylmagnesium chloride in the form of a 20% strength solution in tetrahydrofuran are added dropwise with vigorous stirring at room temperature to a suspension of 61.3 g (0.2 mol) of 3-methyl-1-(5-oxohexyl)-7-propylxanthine in 2 l of anhydrous ether, the internal temperature rising to approximately 30° C. The mixture is then warmed with stirring and under reflux for 2 hours, treated with saturated aqueous ammonium chloride solution to decompose the alkoxide formed, and the organic phase is separated off and washed twice with 500 ml of water each time. The collected water phases are extracted thoroughly with dichloromethane again. The dichloromethane extract is combined with the ethereal phase, dried over sodium sulfate, filtered and evaporated under reduced pressure, 59.0 g of crude product (91.5% of theory) being obtained, which is purified by recrystallization from diisopropyl ether.

Yield:

49.8 g (77.2 % of theory); melting point: 81°–82° C. $C_{16}H_{26}N_4O_3$ (MW=322.4)

| Analysis: | | | |
|---|---|---|---|
| calculated: | C 59.61% | H 8.13% | N 17.38% |
| found: | C 59.72% | H 8.09% | N 17.44% |

EXAMPLE 2

Pharmacological Testing 2.1 Cell Culture

The murine macrophage cell line RAW 264.7 was obtained from ATCC (Rockville, Md.) and cultured in DMEM (Sigma, St. Louis, Mo.) with 4.5 g of glucose/l, 110 mg of sodium pyruvate/l, 10% of heat-inactivated FCS (Gibco, Grand Island, N.Y.) and penicillin/streptomycin (50 U/50 mg/ml).

The macrophages were passaged every 2–3 days and one day before the start of the experiment applied at $2.10^6$ cells to tissue culture flasks (75 $cm^2$, Falcon, Becton Dickinson GmbH, Heidelberg, Germany). The cells were supplied with fresh medium and the preparations were added in the appropriate concentrations. 1-(5-Hydroxy-5-methylhexyl)-3-methyl-7-propylxanthine (compound 1) was dissolved in cell medium at 20 mM. Of this, 100 ml (100 mM) and 50 ml (50 mM) were pipetted into 20 ml of medium. N-(4-Trifluoromethylphenyl)-2-cyano-3-hydroxycrotonamide sodium salt (compound 2) was dissolved in cell medium at 12 mM. Of this, 100 ml each (60 mM final concentration), 33 ml (20 mM final concentration) and 16.7 ml (10 mM final concentration) were pipetted into 20 ml of medium. Stimulation with lipopolysaccharides (LPS; E. coli, serotype 0127: B8 Sigma, St. Louis, Mo.) at a concentration of 10 ng/ml was carried out 1 hour after preincubation with the preparation. Aliquots of a stock solution of lipopolysaccharides (LPS 1 mg/ml in 10% dimethyl sulfoxide (DMSO)) were diluted with medium to a concentration of 1 mg/ml and stored at −20° C. The cells were incubated in 10% $CO_2$ for 24 hours (h) at 37° C.

2.2 Sample preparation

All chemicals used were analytically pure or of electrophoresis quality and were obtained from Millipore Co. (Bedford, Mass.) or Sigma (St. Louis, Mo.), if other sources of supply are not indicated separately.

The 2-D electrophoresis (2-DE) was carried out using the Investigator System® (Millipore), and the samples were worked up according to the procedure of the manufacturer with small changes. The adherent murine macrophages, standing on ice, were washed three times every 60 seconds with 10 ml of ice-cold PBS. The cells were then lysed in 1 ml of boiling lysis buffer, consisting of 0.3 g of SDS, 3.088 g of DTT, 0.444 g of tris HCl and 0.266 g of tris base in 100 ml. The cell lysate was scraped off and heated in boiling water in a 2 ml sample vessel for 10 minutes (min).

Polynucleotides were cleaved at 37° C. in 30 min by addition of Benzonase® (Merck, Darmstadt, Germany).

At this point in the sample preparation, an aliquot was taken, and the protein content was determined by the method of Popov.

For the 2-DE the proteins of the sample were precipitated by dropwise addition to ice-cold acetone (80% v/v). The sample was cooled on ice for 20 min and then centrifuged at 240 g for 10 min. The dried pellet was taken up in one part of lysis buffer and four parts of a sample buffer to give a protein content of 5 mg/ml. The sample buffer consists of 59.7 g of urea, 4.0 ml of NP-40, 1.54 g of DTT, 5.5 ml of carrier ampholyte (pH 3–10, 2-DE optimized) in 100 ml. Undissolved material was separated off before electrophoresis by centrifugation of the samples at 16000×g.

2.3 2-DE gel electrophoresis

High-resolution two-dimensional gel electrophoresis was carried out according to the method of O'Farrell with modifications, such as were described by Garrels. To do this, the Millipore Investigator® 2-D electrophoresis system (Millipore Co., Bedford, Mass.) was employed.

Isoelectric focussing was carried out in glass capillaries (1 mm in diameter) using a 0.08 mm thick fiber which prevents expansion and breaking of the rod.

The IEF gel consists of a 4.1 % T, 2.4% C polyacrylamide matrix which was prepared from a 30.8% T, 2,6% C stock solution, 9.5M urea, 2.0% (v/v) NP-40, 10 mM CHAPS and 2% (v/v) carrier ampholyte (pH 3–10, 2-DE optimized).

0.01M $H_3PO_4$, was used as anode buffer, 0.1M NaOH as cathode buffer. Before the prefocussing to form the pH gradient, 15 ml of a sample coating buffer, consisting of 0.5M urea, 0.2% (v/v) NP-40, 0.1% (v/v) carrier ampholytes and 50 mM DTT, were applied. The voltage maximum of 1500 volts was reached within 90 minutes at a maximum current of 110 mA/gel. After prefocussing, 20 ml of the sample (100 mg of protein) and a further 15 ml of coating buffer were applied.

Isoelectric focussing of the proteins took place within 18000 Vh. After completion of the electrophoresis, the rods were cooled on ice and equilibrated in a buffer consisting of 0.3M tris base, 0.075M tris HCl, 6% SDS, 50 mM DTT and 0.01 % Bromophenol Blue. The rod gels were transferred directly to the surface of the vertical gel of the second dimension or stored at −20° C. until use. The second dimension was carried out in an SDS gradient gel (10–17%) without collecting gel. The gradient was produced by mixing two gel solutions.

A: 100 ml of acrylamide (30.5% T, 1.64% C), 73 ml of tris (1.5M, pH 8.8), 123 ml of $H_2O$, 3 ml of SDS (10%), 150 ml of TEMED and 750 ml of ammonium peroxodisulfate (10%).

B: 170 ml of acrylamide, 73 ml of tris, 66.78 g of glycerol, 3 ml of SDS, 150 ml of TEMED, 750 ml of ammonium peroxodisulfate.

Electrophoresis was carried out overnight at constant temperature in a running buffer consisting of 25 mM tris base, 192 mM glycine and 0.1% SDS until the Bromophenol Blue front was approximately 1 cm removed from the end of the gel. After completion of the electrophoresis, the proteins in the gel were stained with silver reagent according to Heukeshoven and Dernick.

The analysis of the 2-D gels and the preparation of synthetic images were carried out using the Biolmage System (Biolmage Systems Co.). The protein pattern obtained was scanned by a Kodak megaplus camera model 1.4 and the data were processed by a HAM station.

2.4 Results

The results of the unstimulated control were set equal to 100%. The addition of LPS (10 ng/ml) led to a 50% dephosphorylation of cofilin. The simultaneous application of LPS (10 ng/ml) and compound 1 (100 mM) leads to a 10% dephosphorylation of cofilin. The inhibition of dephosphorylation is therefore 80% in comparison with the macrophages only treated with LPS.

Table 1 shows the results. In contrast to 100 mM final concentrations, 50 mM final concentrations of the compound 1 are inactive. Compound 2 is likewise without action up to 20 mM final concentration, it is active only at 60 mM. If compound 1 and compound 2 are combined in a concentration range in which each individual compound is inactive, a superadditive action surprisingly results.

TABLE 1

| RAW 264.7 murine macrophages | Intensity of the cofilin spot (%) | Inhibition of the decrease in intensity (%) |
|---|---|---|
| Control (unstimulated) | 100 | 0 |
| LPS (10 ng/ml) | 50 | 0 |
| LPS + compd. 1 (50 mM) | 50 | 0 |
| LPS + compd. 1 (100 mM) | 55 | 10 |
| LPS + compd. 2 (10 mM) | 50 | 0 |
| LPS + compd. 2 (20 mM) | 50 | 0 |
| LPS + compd. 1 (50 mM)+ compd. 2 (10 mM) | 60 | 20 |
| LPS + compd. 1 (50 mM)+ compd. 2 (20 mM) | 90 | 80 |

What is claimed is:

1. A method for inhibiting the dephosphorylation of the protein cofilin comprising administering to a patient in need thereof a therapeutically effective amount of a compound of the formula I

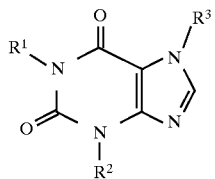

(I)

and/or an optionally stereoisomeric form of the compound of the formula and/or a physiologically tolerable salt of the compound of the formula I,
where
$R^2$ is $(C_1-C_4)$-alkyl,
one of the radicals $R^1$ or $R^3$ is a radical of the formula II

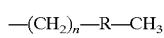

in which
R is
  a) a covalent single bond and in which n is the integer zero, 1, 2, 3, 4, 5, 6 or 7,
  b) a radical —CO— and in which n is the integer 1, 2, 3, 4, 5 or 6, or
  c) a radical —C($R^4$)(OH)— and in which n is the integer 1, 2, 3, 4, 5 or 6 and,
$R^4$ is
  a) a hydrogen atom or
  b) $(C_1-C_3)$-alkyl, and
the other radical $R^3$ or $R^1$ is
  a) a hydrogen atom,
  b) $(C_1-C_7)$-alkyl,
  c) $(C_4-C_8)$-cycloalkylalkyl or
  d) alkyl having 2 to 6 carbon atoms, in which the carbon chain is interrupted by an oxygen atom.

2. The method according to claim 1, wherein
$R^2$ is $(C_1-C_4)$-alkyl, and
one of the radicals $R^1$ or $R^3$ is a radical of the formula II, in which
R is
  a) a radical —CO— or
  b) a radical —C($R^4$)(OH)—,
n is the integer 3, 4, 5 or 6, and
$R^4$ is a hydrogen atom or $(C_1-C_3)$-alkyl, and
the other radical $R^3$ or $R^1$ is $(C_1-C_7)$-alkyl or $(C_4-C_8)$-cycloalkylalkyl.

3. The method according to claim 2, wherein
$R^2$ is $(C_1-C_2)$-alkyl,
$R^1$ is the radical of the formula II, in which
R is
  a) a radical —CO— or
  b) a radical —C($R^4$)(OH)—,
n is the integer 3, 4, 5 or 6, and
$R^4$ is a hydrogen atom or $(C_1-C_2)$-alkyl, and
$R^3$ is $(C_1-C_7)$-alkyl or $(C_4-C_8)$-cycloalkylalkyl.

4. A method according to claim 3, wherein
$R^2$ is $(C_1-C_2)$-alkyl,
$R^1$ is a radical of the formula II, in which
R is
  a) a radical —CO— or
  b) a radical —C($R^4$)(OH)—,
n is the integer 3, 4, 5 or 6, and
$R^4$ is a hydrogen atom or $(C_1-C_2)$-alkyl, and
$R^3$ is $(C_2-C_5)$-alkyl or $(C_4-C_6)$-cycloalkylalkyl.

5. A method according to claim 4, wherein the compound is 1-(5-hydroxy-5-methylhexyl)-3-methyl-7-propylxanthine.

6. A method for inhibiting the dephosphorylation of the protein cofilin comprising administering to a patient in need thereof 1) a therapeutically effective amount of a xanthine derivative of the formula I

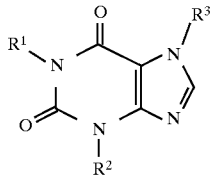

(I)

and/or an optionally stereoisomeric form of the compound of the formula I and/or a physiologically tolerable salt of the compound of the formula I,
wherein
$R^2$ is $(C_1-C_4)$-alkyl,
one of the radicals $R^1$ or $R^3$ is a radical of the formula II

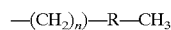

(II)

in which R
  a) is a covalent single bond and in which n is the integer zero, 1, 2, 3, 4, 5, 6 or 7,
  b) is a radical —CO— and in which n is the integer 1, 2, 3, 4, 5 or 6, or
  c) is a radical —C($R^4$)(OH)— and in which n is the integer 1, 2, 3, 4, 5 or 6 and
$R^4$ is
  a) a hydrogen atom or
  b) $(C_1-C_3)$-alkyl, and
the other radical $R^3$ or $R^1$ is
  a) a hydrogen atom,
  b) $(C_1-C_7)$-alkyl,
  c) $(C_4-C_8)$-cycloalkylalkyl or
  d) alkyl having 2 to 6 carbon atoms, in which the carbon chain is interrupted by an oxygen atom;
in conjunctive therapy with 2) a therapeutically effective amount of a compound of the formula IV and/or V,

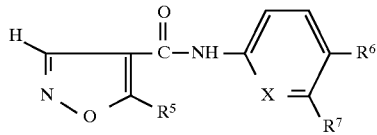 (IV)

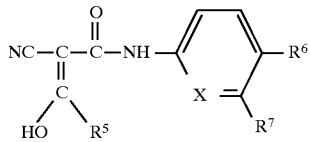 (V)

and/or an optionally stereoisomeric form of the compound of the formula IV or V and/or a physiologically tolerable salt of the compound of the formula IV or V, wherein $R^5$ is
a) $(C_1-C_4)$-alkyl,
b) $(C_3-C_5)$-cycloalkyl,
c) $(C_2-C_6)$-alkenyl or
d) $(C_2-C_6)$-alkynyl, $R^6$ is
a) —$CF_3$,
b) —O—$CF_3$,
c) —S—$CF_3$,
d) —OH,
e) —$NO_2$,
f) halogen,
g) benzyl,
h) phenyl,
i) —O-phenyl,
k) —CN or
l) —O-phenyl, mono- or polysubstituted by 1) $(C_1-C_4)$-alkyl,
2) halogen,
3) —O—$CF_3$ or
4) —O—$CH_3$, $R^7$ is
a) $(C_1-C_4)$-alkyl,
b) halogen, or
c) a hydrogen atom, and X is
a) a —CH group or
b) a nitrogen atom.

7. The method according to claim 6, wherein
$R^5$ is
a) methyl,
b) cyclopropyl, or
c) $(C_3-C_5)$-alkynyl,
$R^6$ is —$CF_3$ or —CN,
$R^7$ is hydrogen or methyl, and
X is a —CH— group.

8. The method according to claim 6, wherein the compound of the formula V is N-(4-trifluoromethylphenyl)-2-cyano-3-hydroxycrotonamide, 2-cyano-3-cyclopropyl-3-hydroxyacrylic acid (4-cyanophenyl)amide or N-(4-trifluoromethylphenyl)-2-cyano-3-hydroxyhept-2-en-6-yne-carboxamide, and the xanthine derivative of the formula I is 1-(S-hydroxy-5-methylhexyl)-3-methyl-7-propylxanthine.

9. The method according to claim 8, wherein the compound of the formula V is N-(4-trifluoromethylphenyl)-2-cyano-3-hydroxycrotonamide, and the xanthine derivative of the formula I is 1-(5-hydroxy-5-methylhexyl)-3-methyl-7-propylxanthine.

* * * * *

UNITED STATES PATENT AND TRADEMARK OFFICE
CERTIFICATE OF CORRECTION

PATENT NO. : 5,856,330
DATED : January 5, 1999
INVENTOR(S) : Müllner et al.

It is certified that error appears in the above-indentified patent and that said Letters Patent is hereby corrected as shown below:

Claim 6, column 12, line 48, "$-(CH_2)_n-R-CH_3$" should read ---$(CH_2)_n-R-CH_3$--.

Signed and Sealed this

Third Day of August, 1999

Q. TODD DICKINSON

*Attest:*

*Attesting Officer*           *Acting Commissioner of Patents and Trademarks*